United States Patent [19]

Minami

[11] Patent Number: 4,596,549
[45] Date of Patent: Jun. 24, 1986

[54] BLOOD DIALYZING METHOD AND APPARATUS

[75] Inventor: Hiromichi Minami, Takarazuka, Japan

[73] Assignee: Nihon Medical Engineering Company, Ltd., Hyogo, Japan

[21] Appl. No.: 687,184

[22] Filed: Dec. 27, 1984

[51] Int. Cl.$^4$ .............................................. A61M 1/34
[52] U.S. Cl. ...................... 604/5; 210/140; 210/321.3; 210/646
[58] Field of Search .............. 604/5, 29; 128/DIG. 3; 210/90, 96.2, 321.3, 140, 646

[56] References Cited

U.S. PATENT DOCUMENTS

| | | | |
|---|---|---|---|
| 3,352,779 | 11/1967 | Austin et al. | 210/321.3 X |
| 3,802,562 | 4/1974 | Kozlov et al. | 210/96.2 |
| 3,844,940 | 10/1974 | Kopf et al. | 210/646 |
| 4,153,554 | 5/1979 | von der Heide et al. | 210/321.3 |

FOREIGN PATENT DOCUMENTS

| | | | |
|---|---|---|---|
| 181162 | 10/1984 | Japan | 604/29 |
| 2001552 | 2/1979 | United Kingdom | 604/5 |

*Primary Examiner*—Anton O. Oechsle
*Attorney, Agent, or Firm*—Koda and Androlia

[57] ABSTRACT

The blood of a patient to be dialyzed is circulated out of the patient's body through an extracorporeal circuit including a blood pump and a dialyzer. The dialyzer has a solution supply piping for the supply of a dialyzing solution thereto and a discharge piping for the discharge of the dialyzing solution therefrom, and the discharge piping is branched into a discharge passage and a metering passage. The supply piping, the discharge passage and the metering passage have disposed thereon a supply control valve, a discharge control valve and a combination of a metering valve and a metering device, respectively. During a washing step, the supply control valve is opened while the discharge and metering control valves are opened and closed, respectively, so that the dialyzing solution within the dialyzer is replenished. During a dialyzing step, only the metering valve is opened so that the water removal can take place in the dialyzer and the quantity of the dialyzing solution increased as a result of the water removal can be measured by the metering device. The washing and dialyzing steps are alternately and cyclically performed.

6 Claims, 11 Drawing Figures

BLOOD DIALYZING METHOD AND APPARATUS

BACKGROUND OF THE INVENTION

The present invention generally relates to the blood dialysis and, more particularly, to a method for the blood dialysis and an apparatus utilizing a dialyzer for the removal of waste products of metabolism from the blood. The method and apparatus herein disclosed according to the present invention are aimed at maximizing the utilization of a dialyzing solution thereby to minimize the consumption of the dialyzing solution.

A technique of blood dialysis by the use of a dialyzer, or an artificial kidney as it is generally known, has long been widely practised to purify the human blood by the removal of waste products of metabolism in the body of a patient suffering from a kidney failure. In this case, the dialyzer functions in lieu of the kidney then failing to function properly.

FIG. 1 of the accompanying drawings illustrate schematically an extracorporeal blood circuit extending from an artery to a vein, for example, from a radial artery to a saphenous vein of a patient A, in which circuit the prior art dialyzing apparatus is placed. The extracorporeal blood circuit shown therein includes an inlet cannula 1a, inserted into the radial artery, and an outlet cannula 1b inserted into the saphenous vein. According to the prior art, the blood to be dialyzed and flowing into the inlet cannula 1a is pumped by a blood pump 2 so as to flow towards a dialyzer unit 3 through a tubing 5a and then towards the outlet cannula 1b through a tubing 5 after having passed through a blood chamber in the dialyzer unit 3. The blood so flowing to the outlet cannula 1b after waste products of metabolism have been removed therefrom is eventually returned to the saphenous vein of the patient A. In addition to the blood chamber, the dialyzer unit 3 has a dialysate chamber communicated through a solution inlet 8a to a source of dialyzing solution on the one hand and through a dialysate outlet 8b to any suitable dialysate disposing container on the other hand. In order to achieve the positive ultrafiltration, that is, in order to create a pressure difference between the flow of the blood within the blood chamber and that of the dialyzing solution within the dialysate chamber to enable the waste products of metabolism contained in the blood to be forced into the dialyzing solution through a membrane within the dialyzer unit 3, the tubing 5 on the downstream side with respect to the direction of flow of the blood towards the outlet cannula 1b has a flow regulator 4 for adjustably constricting the tubing 5. For monitoring the ultrafiltration pressure, a portion of the tubing 5a between the pump 2 and the dialyzer unit 3 and a portion of the tubing 5 between the dialyzer unit 3 and the flow regulator 4 have respective air traps 6a and 6b disposed thereon and fluid-connected with associated pressure gauges 7a and 7b.

When in use for the blood dialysis, the blood pump 2 is operated to effect the extracorporeal circulation of the blood through the extracorporeal blood circuit by way of the dialyzer unit 3 while the flow regulator 4 is adjusted in the light of the readings given by the pressure gauges 7a and 7b to create a proper positive ultrafiltration pressure.

During the blood dialysis so performed, the movement of substances and water by the effect of the osmotic pressure as well as the movement of water by the effect of the ultrafiltration take place within the dialyzer unit. Considering that the water is a substance, it is well known that the movement of the substances within the dialyzer unit has the following relationship:

$$\text{(Velocity of Movement of Substances)} = \frac{\text{Concentration Gradient}}{\text{Resistance}}$$

According to this notion, the velocity of movement of the substances is proportional to the gradient of concentration, but inversely proportional to the resistance to the fluid flow. The resistance to the fluidflow includes not only that given by the semipermeable membrane, which divides the interior of the dialyzer unit into the blood chamber and the dialysate chamber, but also that given by the interlayer of fluid present between one of the opposite surfaces of the semipermeable membrane and the flow of blood within the blood chamber and between the other of the opposite surfaces of the semipermeable membrane and the flow of dialysate within the dialysate chamber. FIG. 2 illustrates an explanatory diagram showing the concentration gradient and the fluid interlayer on each side of the semipermeable membrane. Assuming that the concentration of a certain substance in the blood and that in the dialysate are expressed by $C_B$ and $C_D$, respectively, and the coefficent of mobility of the substances as a whole is expressed by K, the velocity $N_A$ of movement of the substances per unit surface area of the semipermeable membrane can be expressed as follows:

$$N_A = K(C_B - C_D)$$

Also, it is well known that, assuming that the coefficient of mobility of the substances across the fluid interlayer on the side of the blood chamber and that on the side of the dialysate chamber are expressed by $K_B$ and $K_D$, respectively, the coefficient of diffusion of the substances in the semipermeable membrane is expressed by $D_H$, and the thickness of the semipermeable membrane is expressed by L, the resistance 1/K as a whole is equal to the sum of the resistances given by the fluid interlayer confronting the blood chamber, the semipermeable membrane and the fluid interlayer confronting the dialysate chamber, that is, the following relationship can be established (The Journal of the Society of Reserch on Artificial Dialysis, Vol. 2 No. 2, 1969, p98 et seqq.):

$$\frac{1}{K} = \frac{1}{K_B} + \frac{L}{D_H} + \frac{1}{K_D}$$

Accordingly, it can be deduced that, for a dialyzer unit of given design to exhibit an increased dialyzing efficiency, the rate of flow of both of the blood and the dialysate has to be increased to induce a turbulence adjacent the respective surfaces of the semipermeable membrane thereby to reduce the resistances. However, so far as the rate of flow of the dialysate is concerned, the increase of the flow rate to a value as high as permissible may result in the increase of the dialyzing efficiency, which in turn results in the increased consumption of the dialyzing solution. In view of this, in consideration of numerous factors such as the dialyzing efficiency, the dialyzing time and the consumption of the dialyzing solution, the compromise has hitherto been made to supply the dialyzing solution continuously through the dialysate chamber at a rate of about 50 ml/min. Where a plurality of dialyzer units are used, the current practice is either to employ a dialyzing solution supply system for each of the dialyzer units or to employ a large volume dialyzing solution supply system for all of the dialyzer units and, in either case, the total quantity of the dialyzing solution required to be continuously supplied to the dialyzer units amounts to a multiple of the quantity required for each dialyzer unit.

In the conventional method and apparatus for the dialysis, the dialyzing solution is continuously supplied through the solution inlet 8a into the dialysate chamber at which the dialyzing solution is mixed with the substances filtered from the blood chamber through the semipermeable membrane. The dialyzing solution so mixed with the substance, i.e., the waste products of metabolism from the blood, is then discharged continuously as the dialysate from the dialysate outlet 8b. Since a relatively great quantity of the dialyzing solution is accordingly consumed, the conventional method and apparatus require the use of a correspondingly great quantity of both pure water and an undiluted dialyzing liquid to be mixed with the pure water to provide the dialyzing solution. In addition, the heating of the dialyzing solution to a required temperature results in the consumption of a relatively great amount of electric power because of the use of the great quantity of the solution. These disadvantages necessitate the use of a relatively complicated, bulky and expensive device for the preparation and supply of the dialyzing solution.

Apart from the above, with the conventional method and apparatus, in order to comprehend the progress of the removal of excessive water from the blood and also to monitor as to whether the water removal is properly taking place, the amount of water removed has to be metered occasionally during the dialysis. According to the prior art, the measurement of the amount of water removed is carried out in the following manner: Two pumps of equal volume are connected mechanically and inserted respectively in a solution supply piping leading to the solution inlet 8a and in a dialysate discharge piping leading from the dialysate outlet 8b. While the dialyzing solution is supplied through the dialysate chamber at a rate of about 500 ml/min. continously, the flow of about 10 ml/min. is forcibly discharged by the use of a water removal pump of small volume fluid-connected with the dialysate discharge piping through a branch piping to effect a forced water removal in equal quantity. The amount of the water removed is measured in terms of the amount discharged from the water removal pump.

However, with this prior art method, it has been found that the apparatus required to measure the amount of the water removed tends to become complicated and bulky, and since a constant quantity of water is forcibly removed, the patient being dialyzed must be carefully watched for the purpose of safety.

Another prior art method for the measurement of the water removal comprises interrupting the supply of the dialyzing solution for a few minutes per hour, measuring both the amount of water removed during the interruption of the supply of the dialyzing solution for the purpose of sampling and the conditions in which the water removel during the interruption of the supply of the dialyzing solution takes place, and controlling the water removal condition during the normal dialyzing operation on the basis of the result of the measurement so that the total amount of the water removed can be deduced. However, according to this alternative prior art method, the control of the water removal condition is not always easy and the total amount of the water removed is nothing other than the deduced value. Therefore, this alternative prior art method has a disadvantage in that a highly accurate measurement is impossible and, if the accurate measurement were to be achieved, it does not mean that such accurate measurement can be achieved at all times.

In view of the foregoing, the prior art methods for the measurement of the water removed requre the continuous supply of the dialyzing solution through the dialysate chamber of the dialyzer unit so that the whole, or substantially whole, process of dialysis can be performed during the measurement. This is hitherto considered as an essential requirement for the dialysis to be performed and, accordingly, this requirement renders it difficult to perform the measurement of the water removed.

SUMMARY OF THE INVENTION

The present invention has been developed with a view to substantially eliminating the disadvantages and inconveniences inherent in the prior art method and apparatus for the blood dialysis and has for its essential object to provide an improved method and apparatus for the blood dialysis wherein the supply of the dialyzing solution through the dialysate chamber of the dialyzer unit is carried out intermittently during the dialysis performed with the dialyzer unit.

Another important object of the present invention is to minimize the consumption of the dialyzing solution thereby to minimize both the amount of raw material for the dialyzing solution and the amount of energies required to heat, and also to minimize the size of an apparatus used to supply the dialyzing solution.

A further object of the present invention is to achieve an easy and accurate measurement of the amount of excessive water removed to make it possible to administrate the progress of the water removal.

A still further object of the present invention is to systematize the dislyzing apparatus including the dialyzer unit to maximize the utiiZation of the dialyzing solution supply apparatus for supplying the dialyzing solution to a plurality of dialyzer units.

BRIEF DESCRIPTION OF THE DRAWINGS

These and other objects and features of the present invention will become readily understood from the following detailed description taken in conjunction with preferred embodiments of the present invention with reference to the accompanying drawings, in which.

DETAILED DESCRIPTION OF THE EMBODIMENTS

Figure 1:
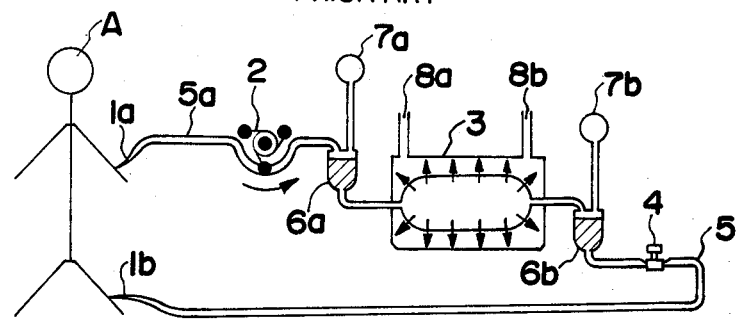
FIG. 1 is a schematic diagram showing the prior art extracorporeal blood circuit including the dialyzing apparatus.
Figure 2:
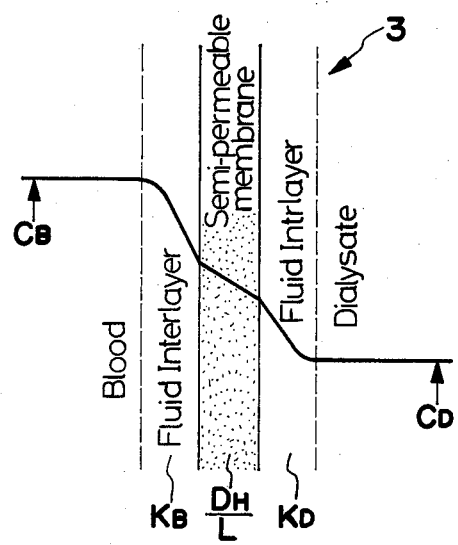
FIG. 2 is a schematic diagram used to explain the principle of dialysis.

Before the detailed description of the present invention proceeds, it is to be noted that like parts are designated by like reference numerals throughout the accompanying drawings.

Figure 3:
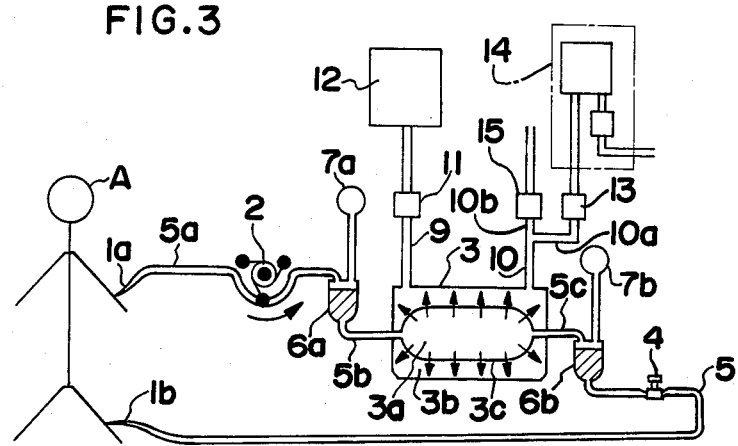
FIG. 3 is a schematic diagram showing an extracorporeal blood circuit including a dialyzing apparatus according to a preferred embodiment of the present invention.

Referring now to FIG. 3, the dialyzer unit 3 is shown to have a blood chamber 3a and a dialysate chamber 3b separated from each other by a semipermeabl membrane 3c. An inlet cannula 1a inserted into the radial artery of a patient A to be dialyzed is fluid-connected through a blood pump 2 by way of a tubing 5a to an air trap 6a which is in turn fluid-connected with the blood chamber 3a through a blood inlet by way of a tubing 5b. The air trap 6a is also fluid-connected with a pressure gauge 7a. On the other hand, the blood, outlet of the dialyzer unit 3 which is in communication with the blood chamber 3a is fluid-connected through a tubing 5c with another air trap 6b having a pressure gauge 7b, which air trap 6b is in turn fluid-connected with an outlet cannula 1b, inserted into the saphenous vein of the patient A, through a tubing 5 by way of an adjustable orifice 4. The extracorporeal circuit so far described is so designed that the blood to be dialyzed and flowing into the inlet cannula 1a is pumped by the blood pump 2 so as to flow towards the blood chamber 3a of the dialyzer unit 3 through the tubing 5a, then the air trap 6a and finally the tubing 5b and then towards the outlet cannula 1b through the tubing 5c, then the air trap 6b and finally the tubing 5 by way of the adjustable orifice 4.

The dialysate chamber 3b of the dialyzer unit 3 has its solution inlet fluid-connected with a source of dialyzing solution 12 through a supply piping 9 having a supply control valve 11 disposed thereon, which solution source 12 may comprise a solution storage tank and a solution pump and which, in the instance now under discussion, is so designed that the dialyzing solution can be supplied into the dialysate chamber 3b under a pressure of about 0.3 to 0.6 kg/cm². It is to be noted that the supply of the dialyzing solution to the dialysate chamber 3b from the solution source 12 can be interrupted when the supply control valve 11 is closed. The dialysate outlet of the dialyzer unit 3 is fluid-connected with a discharge piping 10 having one end in communication with the dialysate chamber 3b and the other end branched into a metering passage 10a and a discharge passage 10b. The metering passage 10a is communicated with a liquid flow meter 14 through a metering control valve 13. On the other hand, the discharge passage 10b is communicated with a solution. recovery tank (not shown) through a discharge control valve 15.

Any one of the supply control valve 11, the metering control valve 13 and the discharge control valve 15 is employed in the form of a normally closed, electromagnetically operated two-way valve which is opened only when electrically energized as will become clear from the subsequent description.

Figure 4:
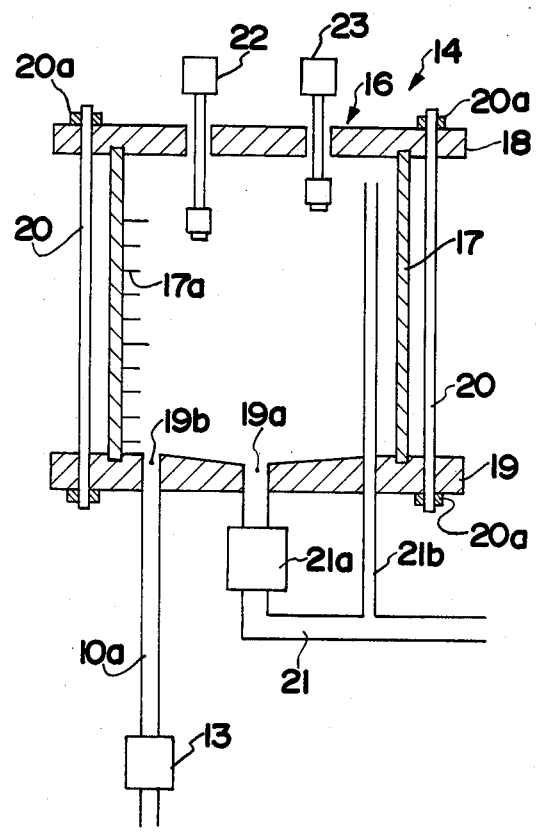
FIG. 4 is a side sectional view of a liquid flow meter employed in the extracorporeal dialyzing circuit shown in FIG. 3.

The details of the liquid flow meter 14 shown in FIG. 3 will now be described with particular reference to FIG. 4. As shown in FIG. 4, the liquid flow meter 14 comprises a generally cylindrical tank 16 constituted by a cylindrical transparent barrel 17 made of heat-resistant glass material and having its opposite open ends tightly closed by top and bottom lids 18 and 19, respectively, said top and bottom lids 18 and 19 being clamped together by means of bolts 20 and nuts 20a with the barrel 17 positioned therebetween. The cylindrical transparent barrel 17 has a row of regularly spaced calibrations 17a embossed, or otherwise printed, thereon so as to extend axially thereof to provide a visual indication of the volume of liquid within the tank 16. The bottom lid 19 has a central area formed with a discharge port 19a which is in communication with a discharge duct 21 having an electromagnetically operated choke valve 21a disposed thereon. The discharge duct 21 may be fluid-connected to any suitable dialysate recovery tank or container (not shown) for collecting the dialysate as will be described later.

To make the dialysate within the metering tank 16 to be discharged completely to the outside of the tank 16 during the opening of the valve 21a, the bottom lid 19 has one of the opposite surfaces facing the top lid 18 which is downwardly sloped so as to converge towards the discharge port 19a as best shown in FIG. 4. An overflow tube 21b having one end communicated with a downstream portion of the discharge duct 21 with respect to the direction of flow of the dialysate towards the dialysate recovery container extends in fluid-tight manner through the bottom lid 19 into the interior of the metering tank 16, terminating at a location spaced a predetermined distance inwardly from the top lid 18. The bottom lid 19 also has a dialysate inlet port 19b defined therein at a location adjacent and inwardly of the transparent cylindrical barrel 17, to which port 19 the metering passage 10a having the metering control valve 13 is fluid-connected.

Referring still to FIG. 4, the top lid 18 carries first and second level switches 22 and 23, the first level switch 22 being activated when the level of the dialysate within the metering tank 16 attains a predetermined level, for example, 100 ml, whereas the second level switch 23 is activated when the level of the dialysate within the metering tank 16 attains a value sufficient for the dialysate to start overflowing into the overflow tube 21b and higher than the predetermined level at which the first level switch 22 is activated.

All of the supply control valve 11, the metering control valve 13 and the discharge control valve 15 are electrically controlled by a control device (not shown) in a timed relationship which will now be described with particular reference to FIG. 5.

Figure 5:
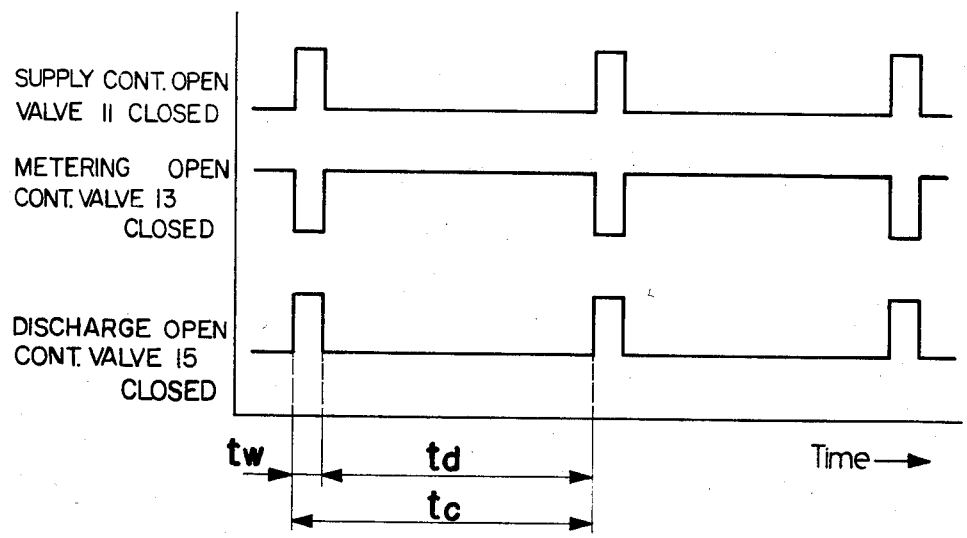
FIG. 5 is a timing chart showing the timed relationship among some flow regulating valves used in the dialyzing circuit shown in FIG. 3.

As shown in FIG. 5, the supply control valve 11 and the discharge control valve 15 are simultaneously opened for a predetermined time cyclically, while the metering control valve 13 is so synchronized with any one of the supply and discharge control valves 11 and 15 as to be opened during the closure of the valves 11 and 13 and closed during the opening of the valves 11 and 13. More specifically, during each cycle time tc, the supply control valve 11 is opened for the predetermined time tw and, at the same time, the metering and discharge control valves 13 and 15 are closed and opened, respectively. During the balance between the cycle time tc and the time tw, that is, during the time td which is greater than the time tw, the metering control valve 13 is opened while both of the supply and discharge control valves 11 and 15 are closed. Accordingly, it is clear that, during the time tw, the dialyzing solution from the solution source 12 past the supply control valve 11 flows through the dialysate chamber 2b of the dialyzer unit 3 and is then discharged to the solution recovery tank (not shown) through the discharge piping 10 and then through the discharge passage 10b by way of the discharge control valve 15. On the other hand, during the time td, no dialyzing solution is supplied into the dialysate chamber 3b of the dialyzer unit 3, but the excessive water removed from the blood, having filtered through the semipermeable membrane 3c into the dialysate chamber 3b, mixes with the dialyzing solution remaining in the dialysate chamber 3b and then flows into the liquid flow meter 14 through the discharge piping 10 and then through the metering passage 10b past the metering control valve 13.

For the purpose of the description of the present invention, the time tw and the time td are hereinafter referred to as a washing step and a dialyzing step, respectively. Then, it will readily be understood that during the washing step the dialyzing solution is allowed to flow through the dialysate chamber 3b of the dialyzer unit 3 to wash it while during the dialyzing step no dialyzing solution is supplied to the dialyzer unit 3, but the dialysis takes place within the dialyzer unit 3 with the consequence that the dialyzing solution, the quantity of which is increasing by the addition of the excessive water filtered through the semipermeable membrane 3c, flows into the liquid flow meter 14. The washing step and the dialyzing steps cyclically alternate with each other.

The details of each of the washing and dialyzing steps will not be described.

As hereinbefore discussed, the presence of the fluid interlayer on each side of and adjacent to the semipermeable membrane constitutes one of the major causes of the lowered dialyzing efficiency. It is the washing step that that is intended to destroy the fluid interlayer thereby to minimize the resistance to the flow of the fluid. Accordingly, the rate of flow of a washing liquid used during the washing step is so selected as to produce a turbulence necessary to destroy the fluid interlayer and, for this purpose, the dialyzing solution to be supplied from the solution source 12 is so pumped as to be supplied to the dialyzer unit 3 under a pressure of about 0.3 to 0.6 kg/cm$^2$. In addition, in order to minimize the resistance to the flow thereby to increase the flow rate, the dialyzing solution used during the washing step is discharged directly through the discharge piping 10, then discharge passage 10b and finally the discharge control valve 15.

The time required to perform the washing step according to the present invention may be of such a relatively short time as to permit the dialyzing solution in a quantity somewhat greater than the dialyzing solution primed into the dialysate chamber in the dialyzer unit 3 to flow for the purpose of replenishing the dialyzing solution. When as a result of the performance of the washing step the resistance given by the fluid interlayer to the flow of the dialyzing solution is reduced, the supply of the dialyzing solution is interrupted, followed by the dialyzing step to permit the transfusion of the substances from the blood chamber into the dialysate chamber within the dialyzer unit 3.

During the dialyzing step, the removal of the excessive water from the blood flowing in the blood chamber takes place through the semipermeable membrane with the quantity of the dialyzing solution within the dialysate chamber consequently increasing. Accordingly, by measuring the increment of the quantity of the dialyzing solution added with the water removed from the blood, the quantity of the water removed from the blood can be measured. For this purpose, during the dialyzing step, the discharge piping 10 leading from dialysate outlet of the dialysate chamber is communicated with the fluid flow meter 14 through the metering passage 10 by way of the metering control valve 13.

During the dialyzing step, however, not only does the transfusion of the excessive water from the blood chamber into the dialysate chamber through the semipermeable membrane take place, but also the fluid interlayer is again formed as the transfusion progresses. Therefore, the washing step described hereinbefore has to be carried out cyclically. According to a series of experiments conducted by the inventors of the present invention with the use of the dialyzer unit of a type requiring 80 ml of dialyzing solution to be primed, it has been found that, when the dialyzing solution heated to about 36° C. was supplied from the solution source 12 under a pressure of about 0.3 kg/cm$^2$ for 3.3 seconds, the total flow of the dialyzing solution was 90 ml. It has also been found that, when the washing step of 3.3 seconds in duration was performed twice during one minute and the remaining seconds of the minute was used for the dialyzing step, that is, when a cycle of the washing and dialyzing steps was performed twice during one minute with the cycle time tc being 30 seconds, the dialyzing efficiency similar to or higher than that exhibited when the dialyzing solution is continuously supplied at a rate of 500 ml/min. could be obtained. However, the time during which the washing step is performed (hereinafter referred to as the washing time) as well as the time during which the dialyzing step is performed (hereinafter referred to as the dialyzing time), that is, how often the washing step should be performed for a given period of time, and the quantity of the washing liquid to be used during the washing step and the washing time, are not always fixed and can be selected depending on and/or in consideration of the performance of the dialyzer unit, the capacity of the solution source to supply the dialyzing solution, the facilities and available manpower at the hospital where the intended dialysis is carried out, and/or the physical condition of the patient to be dialyzed. In addition, although the dialyzing solution has been described as supplied under a pressure of 0.3 to 0.6 kg/cm$^2$, this pressure range may change subject to the specific construction of the dialyzer unit. In any event, important to note in terms of the present invention is that during the interruption of supply of the dialyzing solution to the dialyzer unit, the total, or substantially total, blood dialysis is carried out, and the dialyzer unit is washed by intermittently supplying the dialyzing solution to the dialyzer unit. So far as this is performed without departing the spirit of the present invention, numerous conditions such as, for example, the time factors, the number of cycles and/or the flow rates may be selected to suit to a particular case as desired. With the method according to the present invention, not only can the amount of the dialyzing solution consumed be remarkably reduced, but also both the amount of both of the pure water and the undiluted dialyzing solution required and the amount of electric power consumed can be reduced, making it possible to manufacture the dialyzing apparatus in a compact size.

Hereinafter, the details of the operation of the flow meter 14 will be described.

The electromagnetically operated choke valve 21a is a normally closed valve and, accordingly, as the dialysate (i.e., the dialyzing solution mixed with the water removed from the blood) from the dialyzer unit 3 flows into the metering tank 16 through the dialysate inlet port 19b, the surface level of the dialysate within the metering tank 19 elevates. When the quantity of the dialysate accumulated within the metering tank 16 attains a predetermined quantity, for example, 100 ml. in the instance so far described, the level switch 22 is activated. Upon the activation of the level switch 22, the normally closed choke valve 21a is opened for a predetermined short time to allow the dialysate within the metering tank 16 to be discharged through the discharge duct 21. During the opening of the choke valve 21a for the predetermined short time, the metering control valve 13 is closed to interrupt the flow of the dialysate from the dialyzer unit 3 into the metering tank 16. Each time the choke valve 21a is operated in the manner as hereinabove described, the count given by a counter (not shown) is incremented by one, and accordingly, the result of summation performed by the counter can provie an indication of the total amount of the water removed from the blood, it being to be noted that the count of one (1) corresponds to a unit of 100 ml of the water removed. In addition, the reading of the calibrations 17a can back up the accuracy of the measurement of the amount of the water removed which is performed by the counter. In the event that the top surface of the dialysate within the metering tank 16 exceeds a maximum limit determined in consideration of the available volume of the metering tank 16 by reason of the failure of the choke valve 21a to operate properly, the dialysate within the metering tank 16 starts overflowing into the overflow tube 21b and then into the discharge duct 21 on the one hand and the level switch 23 is activated to energize a warning lamp and/or a warning buzzer on the other hand to alarm the attendant operator of an abnormal condition occurring in the system. If necessary, means may be provided to close the metering control valve 13 in response to the activation of the level switch 23 thereby to interrupt the removal of the excessive water from the blood.

By the use of the fluid flow meter 14 of the construction described above, the total quantity of the water removed from the blood during the dialyzing steps can be measured. Although the fluid flow meter 14 is simple in structure, it is possible to accurately measure the total quantity of the water removed from the blood.

With respect to the washing step, it can hardly be considered that the water removal takes place during each washing step because the dialyzing solution is supplied under a relatively high pressure as hereinbefore described, and what is more, the duration of each washing step is selected to be far shorter than that of each dialyzing step. Therefore, the quantity of the water removed from the blood during each washing step, if any, can be neglected, without the measurement of the quantity of the water removed being detrimentally affected. Should the quantity of the water removed during each washing step be not neglected, or should the highly accurage measurement be required, the following procedure may be taken. With the use of time counters for the measurement of the respective durations during which the metering control valve 13 and the discharge control valve 15 are operated, i.e., opened, the quantity of the water removed from the blood per unit time is calculated on the basis of the duration of the opening of the metering control valve 13 and the reading of the calibration 17a aligned with the level of the dialysate within the metering tank 16 and the product of both of the quantity of the water removed per unit time and the duration of opening of the discharge control valve 15 multiplied by a suitable coefficient is then added to the quantity of the water removed which has been indicated by the reading of the calibration 17a. In this method, the dialyzing apparatus may include respective display units for providing a visual indication of the times during which the valves 13 and 15 are opened, respectively, so that the operator of the system can perform the required calculation, or it may include a microcomputer in combination with suitable sensors so that the required calculation can automatically be performed with the result of the calculation being displayed by a display unit and at the same time, the progress of the dialyzing process can be automatically monitored. By way of example, the system may be so designed that, when the speed of the water removal being performed starts lowering a predetermined value, the dialyzing step can be switched over to the washing step, or when the speed of the water removal being performed starts increasing over the predetermined value or when the total amount of the water removed attains a predetermined value, the water removal can be interrupted.

Figure 6:
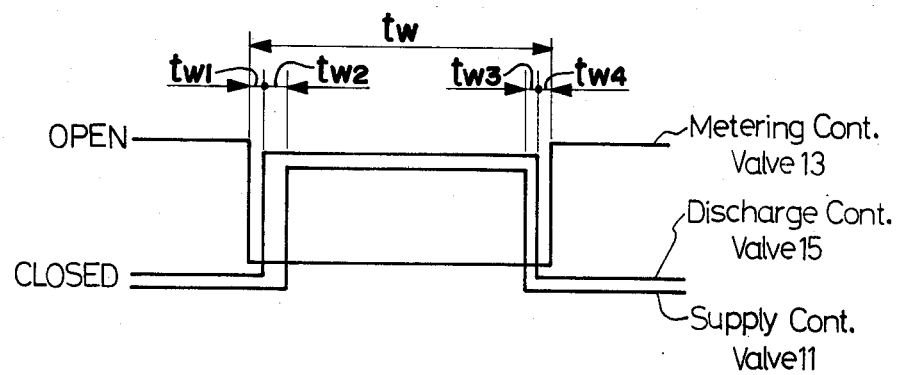
FIG. 6 is a timing chart showing the timed relationship among the flow regulating valves shortly before the washing step.

In the foregoing description, the control valves 11, 13 and 15 have been described as simultaneously controlled to effect the washing and dialyzing steps alternately in the manner as shown and described with particular reference to the chart of FIG. 5. However, they may be controlled in a delayed manner as will now be described with particular reference to FIG. 6. Referring now to FIG. 6, the control valves 11, 13 and 15 are so programmed that the discharge control valve 15 can be opened a predetermined time $tw_1$ after the closure of the metering control valve 13 to establish the washing step, followed by the opening of the supply control valve 11 which takes place a predetermined time $tw_2$ after the opening of the metering control valve 13 and that, when the washing step is to be switched over to the dialyzing step, the discharge control valve 15 can be closed a predetermined time $tw_3$ after the closure of the supply control valve 11, followed by the opening of the metering control valve 15 which takes place a predetermined time $tw_4$ after the closure of the discharge control valve 15. According to the program shown in FIG. 6, there is no possibility that the metering control valve 13 is opened simultaneously with the other two control valves, particularly the supply control valve 11, and accordingly, no dialyzing solution except for the water removed from the blood, that is, except for the dialysate, will not flow into the metering tank 16 at all. The predetermined delay times $tw_1$, $tw_2$, $tw_3$ and $tw_4$ can be selected to be within the range of several fractions of a second depending on the response speed of each of the control valves 11, 13 and 15 and may, for examples, be 0.2 second, 0.5 second, 0.2 second and 0.2 second, respectively.

Referring back to FIG. 3, the apparatus shown therein is such that during the dialyzing step both of the supply control valve 11 and the discharge control valve 15 are closed while the metering control valve 13 is opened. However, arrangement has been made that, in the event of the occurrence of an abnormal condition in the course of the dialyzing step, the metering control valve 13 can also be closed to confine the dialyzing solution within the system and no water removal takes place. The abnormal condition referred to above includes the possibility wherein, as a result of, for example, the excessive removal of the water from the blood, the patient being dialyzed is likely to suffer from an undesirable drop in blood pressure or the like. The inventors of the present invention have previously proposed one method for detecting such an abnormal condition, which method is a subject matter of the Japanese Patent Application No. 58-57147 and can be applicable in the practice of the present invention. If the method for detecting the abnormal condition disclosed in the above described application is employed in the practice of the present invention, not only can the safety factor of the system be increased, but the minimized utilization of energies can also be accomplished. In any event, the detection of the occurrence of the abnormal condition can be accomplished by the use of an air trap on the tubing $5b$ between the inlet cannula $1a$ and the blood pump 2 in combination with a pressure gauge for detecting the blood pressure at the air trap so that, when the blood pressure so detected falls below a predetermined value, the metering control valve 13 can be forcibly closed. In this way, a precaution can be taken to avoid the drop in blood pressure resulting from the excessive water removal thereby to facilitate a stabilized and efficient dialysis and, therefore, not only can the patient being dialyzed be protected, but also the minimized utilization of the energies can be achieved. It is to be noted that, even during the closure of the metering control valve 13 accompanied by the interruption of the water removal in the event of the occurrence of the abnormal condition, the transfusion of the substances from the blood into the dialyzing solution takes place by the action of the osmotic pressure and, accordingly, it is desirable to carry out the washing step similarly even in this case. As a matter of course, however, in the event of the occurrence of the abnormal condition that requires the system to be brought to a complete halt, a precaution appropriate to such abnormal condition should be taken.

Although in describing the foregoing embodiment according to the present invention reference has been made to the use of the only dialyzer unit 3, the concept of the present invention can equally be applicable to the case wherein a plurality of dialyzer units are utilized to carry out the dialysis subject to a corresponding number of patients simultaneously. In such case, either a single solution source or a plurality of solution sources may be employed for all of the dialyzer units and the supply of the dialyzing solution to the dialyzer units may be systematized so as to be controlled by a microcomputer. In any event, the embodiment wherein a plurality of dialyzer units are employed will be hereinafter described with particular reference to FIG. 7, it being to be noted that only one solution source is employed as shown by $12a$.

Figure 7:
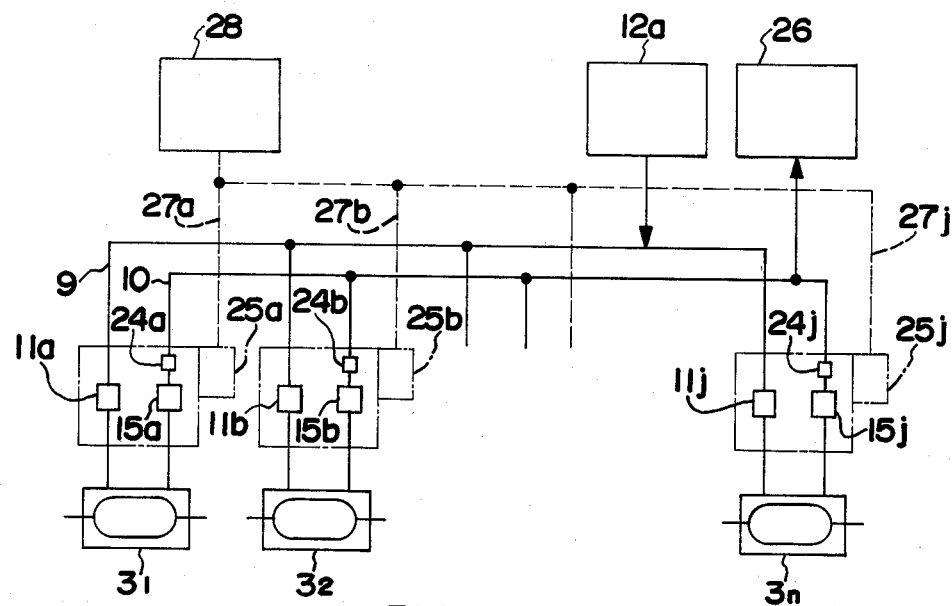
FIG. 7 is a diagram showing another embodiment of the present invention wherein a plurality of dialyzer units are employed.

Referring now to FIG. 7, the dialyzer units are indicated by $3_1, 3_2 \ldots$ and $3_n$ having their respective dialysate chambers fluid-connected with the common source $12a$ of the dialyzing solution through supply pipings 9 on the one hand and with a common discharge container 26 through discharge pipings 10 on the other hand. Although not shown in FIG. 7, the dialyzer units $3_1, 3_2 \ldots$ and $3_n$ also have their blood chambers forming respective parts of the extracorporeal blood circuits associated with individual patients equal in number to the number of the dialyzer units employed.

The supply pipings 9 have respective supply control valves $11a, 11b \ldots$ and $11j$ whereas the discharge pipings 10 have respective discharge control valves $15a, 15b \ldots$ and $15j$ and respective flow sensors $24a, 24b \ldots$ and $24j$ each located on one side of the associated discharge control valve $15a, 15b \ldots$ or $15j$ remote from the associated dialyzer unit $3_1, 3_2 \ldots$ or $3_n$. A set of one of the supply control valves $11a, 11b$ and $11j$, the respective discharge control valve $15a, 15b \ldots$ or $15j$ and the respective flow sensor $24a, 24b$ or $24j$ for each dialyzer units $3_1, 3_2 \ldots$ or $3_n$ are accommodated within an associated control console $25a, 25b \ldots$ or $25j$ which is positioned adjacent a respective patient's bedside together with the associated dialyzer unit. Each of the flow sensors $24a, 24b \ldots$ and $24j$ is used to detect the flow of the dialyzing solution and may comprise an ultrasonic flow sensor available in the commercial market.

The bedside control consoles $25a, 25b \ldots 25j$ are electrically connected with a central control console 28 through respective lines $27a, 27b \ldots$ and $27j$. The central control console 28 is provided with a signal generator or transmitter (not shown) capable of outputing a command signal So on a time sharing basis to the individual bedside control consoles $25a, 25b \ldots$ and $25j$ to initiate the washing step, each of said bedside control console $25a, 25b \ldots$ and $25j$ being so designed as to cause the washing step to be carried out so long as the command signal is supplied to the associated bedside control console $25a, 25b \ldots$ or $25j$. Although not shown, each of the bedside control consoles $25a, 25b \ldots$ or $25j$ is provided with a timer for adjusting the duration during which the washing step is performed, which timer can be adjustable within the range of time allocated to such bedside control console $25a, 25b \ldots$ or $25j$.

Figure 8:
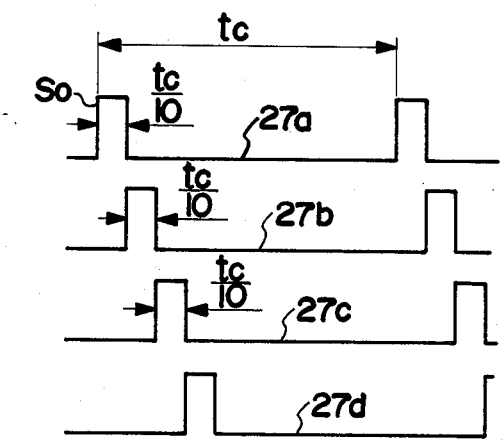
FIG. 8 is a chart showing the timed relationship among electric signals generated from a central control panel employed in the fluid circuit shown in FIG. 7.
Figure 8:
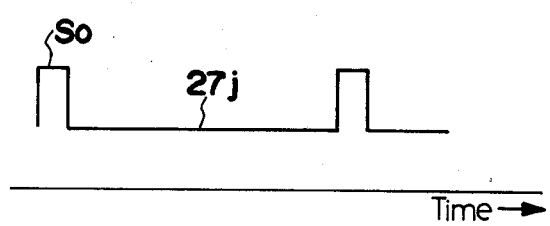
Figure 9:
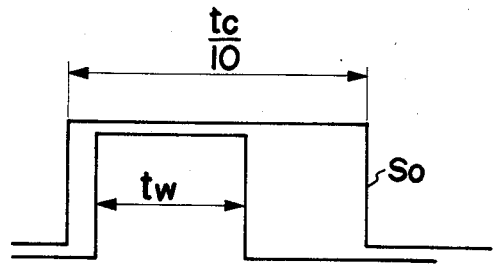
FIG. 9 is a chart showing the relationship between the washing step and an electric signal used to initiate the washing step in one of the dialyzer units.
Figure 10:
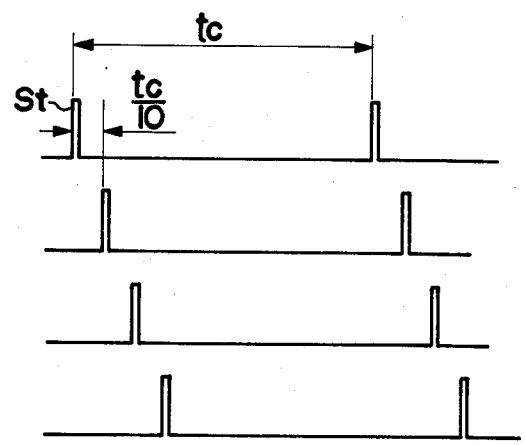
FIG. 10 is a chart showing the timed relationship among the electric signals used to initiate the washing step in thedialyzer units, which signals are used as trigger signals.
Figure 11:
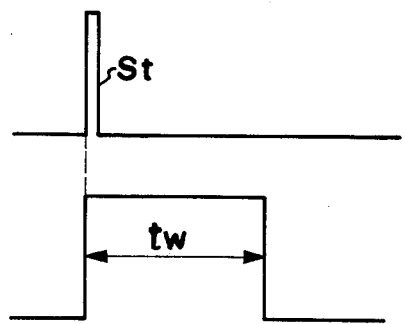
FIG. 11 is a chart showing the timed relationship between the trigger signal and the washing step.

FIG. 8 illustrate the waveforms of the command signals So fed to the respective bedside control consoles $25a$ to $25j$ through the associated lines $27a$ to $7j$ and it will readily be seen that the respective states of the command signals So outputed through the associated lines $27a$ to $27j$ change successively with the passage of time while the duration of one tenth of the cycle time tc is allocated to each of the bedside control consoles $25a$ to $25j$. FIG. 9 illustrates the relationship between one of the command signal So and the associated timer in the respective bedside control console $25a, 25b \ldots$ or $25j$ and it will readily be seen that the time tw during which the washing step is performed and which is determined by the associated timer falls within the duration of one tenth of the cycle time tc. Accordingly, each of the supply control valves $11a, 11b \ldots$ and $11j$ is opened only during the time tw to permit the dialyzing solution to be supplied from the common source $12a$ to the respective dialyzer unit $3_1, 3_2 \ldots$ or $3_n$ so that the washing step can be performed. On the other hand, each of the discharge control valves 15a, 15b . . . and 15j is opened at all times so that the dialyzing solution containing the dialysate filtered in the associated dialyzer unit $3_1$, $3_2$ . . . or $3_n$ can flow therethrough during the dialyzing step and, during the washing step, the dialyzing solution supplied through the supply control valve 11a, 11b or 11j can flow therethrough. Each of the flow sensors 24a to 24j operates during the washing step to detect whether or not a predetermined quantity of the dialyzing solution has flown therethrough and to generate a warning signal, which may be utilized to activate a suitable alarming device, in the event that the predetermined quantity of the dialyzing solution has failed to flow therethrough.

However, each of the discharge control valves 15a to 15j is adapted to be closed in the event of and during the occurrence of the abnormal condition such as, for example, the abrupt drop in blood pressure of the respective patient being dialyzed, to interrupt the water removal. Even in this case, the washing step takes place cyclically in the manner as hereinbefore described in connection with the foregoing embodiment of the present invention. Although the flow meter, shown by 14 in FIG. 3, for each of the dialyzer units $3_1$ to $3_n$ is not illustrated in FIG. 7, it may be employed if desired or required in association with the respective dialyzer unit $3_1$, $3_2$ . . . or $3_n$ and, in such case, each of the discharge control valves 15a to 15j has to be controlled in a manner similar to that described in connection with the foregoing embodiment.

In any event, in the embodiment of the present invention shown in FIG. 7, the supply control valves 11a to 11j are successively opened one after another in response to the respective command signals So outputed from the central control console 28 and, accordingly, the dialyzing solution is supplied to the dialyzer units $3_1$ to $3_n$ on a time sharing basis, that is, at different, but succeeding timings. The time during which the washing step is to be performed in each of the dialyzer units can be adjusted by the timer provided in the associated bedside control console 25a, 25b . . . or 25j depending on the physical condition of the associated patient to be dialyzed. Accordingly, where one or some of the dialyzer units are not desired to be used, the associated timer or timers have to be zeroed to keep them in operative position.

In view of the foregoing, despite the fact that the dialyzing solution is supplied to the dialyzer units $3_1$ to $3_n$, the total quantity of the dialyzing solution required to be supplied to all of the dializer units can be reduced considerably and, concurrently, the flow of the dialyzing solution per unit time can advantageously be averaged. Therefore, the utilization of the source of the dializing solution, shown by 12a, can be maximized remakably. As, described above, with the system according to the present invention, not only can the amount of the dialyzing solution consumed be advantageously reduced, but both the construction and the piping arrangement of the dialyzing solution source 12a can also be simplified with the consequence that the manufacturing cost of the apparatus as a whole is considerably reduced. By way of example, whereas the conventional apparatus requires the continuous supply of the dialyzing solution at a rate of 500 ml/min per dialyzer unit and, if the number of the dialyzer units is 10, the conventional solution supply device for supplying the dialyzing solution to these ten dialyzer units must have a capacity of supplying it at a rate of 5,000 ml/min for all of the dialyzer units, the solution supply device, i.e., solution source 12a, employed in the present invention suffices to have a capacity of supplying the dialyzing solution at a rate of 1,000 ml/min for an equal number of the dialyzer units $3_1$ to $3_n$ provided that the cycle time tc be fixed at 60 seconds and a single washing step performed in each dialyzer unit requires the supply of the dialyzing solution at a rate of 100 ml/min. Thus, comparing with the conventional solution supply device, the solution supply device forming the solution source 12a in the present invention has the solution supplying capacity which is one fifth of that of the conventional one. Where the cycle time tc employed in the present invention is shortened to 30 seconds and 20 seconds, it has been found that the amount of the dialyzing solution consumed is 2,000 ml/min and 3,000 ml/min, respectively, which is smaller than that in the conventional apparatus. The determination of the cycle time, however, depends on the facilities and manpower available in the hospital, the physical condition of the individual patients and other factors known to those skilled in the art, and can be carried out by the adjustment of the cycle of the generator or transmitter employed in the central control console 28 for outputing the command signals So.

In describing the embodiment of the present invention shown in and with reference to FIG. 7, reference has been made to the employment of the only solution source 12a for all of the dialyzer units $3_l$ to $3_n$. However, it is an obvious expedient to those skilled in the art to employ two or more solution sources for two to more groups of the dialyzer units or to employ the solution sources equal in number to the number of the dialyzer units employed.

Each of the bedside control consoles 25a to 25j employed in the embodiment shown in FIG. 7 is provided not only with the respective timer for setting the time during which the washing step is to be performed with reference to an associated calibrated dial, but also with coupling ports for the connection with the supply and discharge pipings 9 and 10, respectively, a display lamp for providing a visual indication that the washing step is being performed, a combination of a display lamp and a warning buzzer for providing visual and audio indications of the occurrence of the abnormal condition, and a manipulatable On-Off button for the warning buzer. Where the fluid flow meter is used for each of the dialyzer units, the associated bedside control console has to be provided with a display device for the display of the quantity of the dialyzing solution, a resetting button for zeroing the display given by the display device, a setting device for setting a predetermined quantity of the water to be removed, and other instruments. Moreover, it may be provided with a protective device for avoiding any possible excessive water removal, and any other instruments considered necessary. Although in the instance shown in FIG. 7, the central control console 28 is shown and described as separate from any one of the bedside control consoles 25a to 25j, it may be built in one of the bedside control consoles 25a to 25j.

Furthermore, although in the embodiment shown in FIG. 7 the dialyzing solution has been described as intermittently supplied to all of the dialyzer units $3_l$ to $3_n$ on the time sharing basis, arrangement may be made to supply any one of the liquids such as sterilizing solution, cooling liquid and rinsing liquid to any one of the dialyzer units on a time sharing basis in a manner similar to the supply of the dialyzing solution. More specifically, arrangement may be made such that, prior to the supply of the dialyzing solution for the performance of the dialysis, the dialyzer units can be washed with pure water, sterilized with hot water or sterilizing solution and cooled with the dialyzing solution, and a similar washing and sterilization of the dialyzer units can be performed even after the termination of the dialysis. Whereas according to the prior art, liquid is continuously supplied during each of the steps, in the present invention the respective liquids are intermittently supplied during each of the steps preferably at a relatively high rate and, yet, on a time sharing basis so that the amount of each of the liquids consumed can advantageously reduced considerably.

As hereinbefore fully described, the present invention is advantageous in that the measurement of the amount of the water removed can be performed in a simplified manner with the use of the flow meter of the construction described with reference to and shown in FIG. 4. However, the flow meter may not be limited to the construction shown in FIG. 4, but any other flow meter can be employed in the practice of the present invention. By way of example, an integrating flowmeter of volume type may be employed to measure the rate of flow of the fluid through the metering passage 10a. Alternatively, the discharge piping 10 may be provided with an ultrasonic flow sensor for measuring the rate of flow of the fluid therethrough, in combination with an integrator for integrating the output generated from such flow sensor during the dialyzing step.

Although the present invention has fully been described in connection with the preferred embodiments thereof with reference to the accompanying drawings provided only for the purpose of illustration, it should be noted that various changes and modifications are readily conceivable to those skilled in the art without departing from the true scope and spirit of the present invention as defined by the appended claims. Such changes and modifications are to be included within the scope of the present invention.

What is claimed is:

1. A method for blood dialysis performed by the use of at least one dialyzer characterized in that the supply of dialyzing solution to the dialyzer is carried intermittently, a plurality of dialyzers are employed and the supply of dialyzing solution from at least one source of the dialyzing solution is performed on a time sharing basis.

2. An apparatus for carrying out the blood dialysis by the use of at least one dialyzer characterized in that there is provided a solution supply control valve on a solution supply piping for the supply of a dialyzing solution to the dialyzer, said solution supply control valve being closed during the performance of blood dialysis to interrupt the supply of the dialyzing solution to the dialyzer, but being controlled so as to open intermittently, dialyzing solution being supplied to the dialyzer during the intermittent opening of the solution supply control valve and a discharge piping leading from the dialyzer is branched to provide a metering passage and a discharge passage, said metering passage having a measuring device for the measurement of the quantity of the dialyzing solution flowing therethrough, said discharge passage bypassing said metering device, said metering and discharge passages being provided respectively with a metering control valve and a discharge control valve, said metering control valve and said discharge control valve being opened and closed, respectively, during the closure of the solution supply control valve, but being closed and opened, respectively, during the opening of the solution supply control valve.

3. An apparatus as claimed in claim 2, wherein even during the closure of the solution supply control valve, said metering control valve is closed in the event of occurrence of an abnormal condition.

4. An apparatus as claimed in claim 2, wherein said measuring device comprises a container for the temporary storage of the dialyzing solution, a level switch adapted to be activated when the quantity of the dialyzing solution within the container attains a predetermined level, a discharge duct extending exteriorly of the container from the bottom thereof, and a choke valve disposed on the discharge duct and adapted to be opened in response to an output signal, which is generated from the level switch when activated, to allow the predetermined quantity of the dialyzing solution within the container to be discharged out of the container, and further comprising a counting means for counting the number of times during which the choke valve is opened.

5. An apparatus for carrying out the blood dialysis, which comprises a common source of dialyzing solution, a plurality of dialyzers fluid-connected with said common solution source through respective supply pipings, a solution supply control valve disposed on each of the supply pipings, and a signal generator for generating pulse signals to the respective solution supply control valves on a time sharing basis, each of said solution supply control valves being opened in response to the associated pulse signal for a predetermined time.

6. An apparatus as claimed in claim 5, wherein each of said solution supply control valves is opened during the duration of the associated pulse signal and for a predetermined time determined for each of the solution supply control valves.

* * * * *